United States Patent
Colen et al.

(10) Patent No.: US 11,446,084 B2
(45) Date of Patent: Sep. 20, 2022

(54) LASER DRILLING OF PIA MATER

(71) Applicant: Neuralink Corp., Fremont, CA (US)

(72) Inventors: Dalton James Colen, San Francisco, CA (US); Shivani Shah, San Francisco, CA (US)

(73) Assignee: Neuralink Corp., Fremont, CA (US)

( * ) Notice: Subject to any disclaimer, the term of this patent is extended or adjusted under 35 U.S.C. 154(b) by 24 days.

(21) Appl. No.: 16/924,063

(22) Filed: Jul. 8, 2020

(65) Prior Publication Data

US 2021/0007803 A1 Jan. 14, 2021

Related U.S. Application Data

(60) Provisional application No. 62/873,422, filed on Jul. 12, 2019.

(51) Int. Cl.
*A61B 18/20* (2006.01)
*A61B 18/00* (2006.01)

(52) U.S. Cl.
CPC .... *A61B 18/20* (2013.01); *A61B 2018/00446* (2013.01); *A61B 2018/00577* (2013.01); *A61B 2018/00589* (2013.01); *A61B 2018/00625* (2013.01); *A61B 2018/2005* (2013.01)

(58) Field of Classification Search
CPC ............ A61B 18/20; A61B 2018/2005; A61B 2018/00589; A61B 2018/00625; A61B 2018/00577; A61B 2018/00446
See application file for complete search history.

(56) References Cited

U.S. PATENT DOCUMENTS

| | | |
|---|---|---|
| 2002/0087201 A1 | 7/2002 | Firlik et al. |
| 2003/0088274 A1 | 5/2003 | Gliner et al. |
| 2003/0088301 A1 | 5/2003 | William |
| 2003/0097161 A1 | 5/2003 | Firlik et al. |
| 2003/0130577 A1 | 7/2003 | Purdy et al. |
| 2003/0232198 A1 | 12/2003 | Lamberti et al. |
| 2003/0232746 A1 | 12/2003 | Lamberti et al. |
| 2004/0014211 A1 | 1/2004 | Ogle et al. |
| 2005/0021105 A1 | 1/2005 | Firlik et al. |
| 2005/0021107 A1 | 1/2005 | Firlik et al. |
| 2005/0042227 A1 | 2/2005 | Zankel et al. |
| 2005/0048047 A1 | 3/2005 | Kakkis |
| 2006/0051322 A1* | 3/2006 | Tuszynski ............... A61P 25/02 424/93.2 |
| 2006/0190056 A1 | 8/2006 | Gliner et al. |
| 2006/0195155 A1 | 8/2006 | Firlik et al. |
| 2007/0148633 A1 | 6/2007 | Sakezles |
| 2008/0026462 A1 | 1/2008 | Ogle et al. |
| 2008/0145404 A1 | 6/2008 | Hill et al. |
| 2008/0213179 A1 | 9/2008 | Gaillard et al. |

(Continued)

FOREIGN PATENT DOCUMENTS

WO WO-2020180696 A1 * 9/2020 ............. B23K 26/50

*Primary Examiner* — Gary Jackson
*Assistant Examiner* — Sebastian X Lukjan
(74) *Attorney, Agent, or Firm* — Kilpatrick Townsend & Stockton LLP

(57) ABSTRACT

The disclosure provides an apparatus and methods for performing a piotomy on a mammal comprising: performing a craniotomy to remove the skull and expose dura mater; removing the dura mater and arachnoid mater to expose subarachnoid space; and performing a piotomy using a laser to create a hole and expose the cerebral cortex.

18 Claims, 3 Drawing Sheets

(56) References Cited

U.S. PATENT DOCUMENTS

| | | |
|---|---|---|
| 2009/0076357 A1 | 3/2009 | Purdy |
| 2009/0123547 A1 | 5/2009 | Hill et al. |
| 2009/0124552 A1 | 5/2009 | Hill et al. |
| 2009/0171416 A1 | 7/2009 | Firlik et al. |
| 2009/0259275 A1 | 10/2009 | Wan |
| 2009/0275927 A1* | 11/2009 | Fein ............... H01S 3/2232 606/3 |
| 2010/0028370 A1 | 2/2010 | Zankel et al. |
| 2010/0166281 A1 | 7/2010 | Buerger et al. |
| 2010/0179518 A1 | 7/2010 | Ludvig et al. |
| 2010/0226961 A1 | 9/2010 | Lamberti et al. |
| 2010/0262036 A1 | 10/2010 | Najafi et al. |
| 2010/0324397 A1 | 12/2010 | Purdy |
| 2011/0021885 A1 | 1/2011 | Ma et al. |
| 2011/0177170 A1 | 7/2011 | Bryukhovetskiy et al. |
| 2012/0046531 A1 | 2/2012 | Hua |
| 2012/0053506 A1 | 3/2012 | Ludvig et al. |
| 2012/0076868 A1 | 3/2012 | Lamberti et al. |
| 2012/0276510 A1 | 11/2012 | Sakezles |
| 2012/0321597 A1 | 12/2012 | Hill et al. |
| 2013/0149318 A1 | 6/2013 | Reynolds et al. |
| 2013/0274846 A1 | 10/2013 | Lad et al. |
| 2014/0045748 A1 | 2/2014 | Hong |
| 2014/0271601 A1 | 9/2014 | Aimetti et al. |
| 2014/0335054 A1 | 11/2014 | Gao et al. |
| 2015/0038948 A1 | 2/2015 | Ludvig et al. |
| 2015/0045766 A1 | 2/2015 | Ludvig et al. |
| 2016/0303171 A1 | 10/2016 | Tseng et al. |
| 2017/0096683 A1 | 4/2017 | Scaria et al. |
| 2018/0344329 A1* | 12/2018 | Najafi Haeri ...... A61B 17/1739 |

\* cited by examiner

LASER DRILLING OF PIA MATER

CROSS-REFERENCES TO RELATED APPLICATIONS

This application claims priority to U.S. Provisional application 62/873,422, filed Jul. 12, 2019, the teachings of which is incorporated hereby reference in its entirety for all purposes.

BACKGROUND

In general, to gain access to the brain such as during neurosurgery, exposure begins by removal of parts of the bones making up the skull while performing a craniotomy. Removal of parts of the skull allows access to areas of the brain, and careful manipulation of tissues allows access to structures deep within the brain.

After the skull is removed, the dura mater is removed to expose the subarachnoid space. The subarachnoid space is a compartment that contains the body of the spinal cord and CSF, which is a fluid that fills and surrounds the ventricles of the brain and the spinal cord and acts as a lubricant and a mechanical barrier against shock.

Approaches to implanting implantable electrodes into neurological tissue such as the brain include the "sewing machine" method and device disclosed in WO 2016/126340. The methods and systems disclosed therein include implantable electrode devices, which comprise (i) a biocompatible substrate, (ii) a conduit (e.g., an electrode, a waveguide) that is disposed on the biocompatible substrate, and (iii) an engagement feature (e.g., a loop) for reversible engagement with an insertion needle. The implantable electrode is implanted using an insertion needle that includes an engagement feature corresponding to the engagement feature of the implantable electrode. To implant, the electrode is reversibly engaged with an insertion needle, the insertion needle is inserted into a biological tissue (e.g., to a desired depth), and the insertion needle is retracted, thereby disengaging the implantable electrode and allowing the electrode to remain implanted in the biological tissue.

The pia mater is the layer of the brain below the arachnoid space and above the cerebral cortex. Inserting a needle using the sewing machine through the pia mater is difficult. A method to remove the pia mater would create one less barrier for a clean insertion of a needle and an electrode into the cerebral cortex.

Accordingly, there remains a need for an apparatus and method for removal of pia mater before needle and/or electrode insertion. The present disclosure satisfies these needs as well as related advantages by providing an apparatus and method to remove pia mater for easier insertion of cerebral electrodes and other applications.

BRIEF SUMMARY

In one embodiment, the present disclosure provides a method for performing a piotomy on a mammal, the method comprising:

performing a craniotomy to remove the skull and expose dura mater;

removing the dura and arachnoid mater to expose subarachnoid space; and performing a piotomy using a laser to create a hole and expose the cerebral cortex.

In one aspect, the mammal is a non-human primate.
In one aspect, the mammal is a human.

In one aspect, the laser has a wavelength of about a 350 nm to about 10.6 µm.

In one aspect, the laser is a 2 µm wavelength laser.

In one aspect, the laser vaporizes water in the pia mater to ablate the tissue and create a hole.

In one aspect, the laser is a pulsed powered laser.

In one aspect, the pulse has a width (length) of about 10 nanoseconds to about 50 nanoseconds. A nanosecond is $10^{-9}$ second.

In one aspect, there is a 30-500 millisecond (ms) pulse train of 10 nanoseconds to about 50 nanoseconds pulses. In one aspect, there is 208 ms of 30 ns pulses.

In one aspect, the pulse has a frequency of about 10 kHz to about 50 kHz.

In one aspect, the laser source has average power delivery of about 0.5 watt to about 15 watts, such as 10.5 watts.

In one aspect, the subarachnoid space is suctioned or otherwise dried before performing the piotomy using the laser.

In another embodiment, the disclosure provides a method for performing a piotomy on a mammal, the method comprising:

performing a craniotomy to remove the skull and expose dura mater;

removing the dura mater and arachnoid mater to expose subarachnoid space; and performing a piotomy using a laser, to create a hole and expose the cerebral cortex, wherein the laser vaporizes water in the pia mater to ablate the tissue to create the hole.

Advantageously, performing a piotomy using a laser to create a hole and expose the cerebral cortex allows for insertion of implantable devices such as a needle in brain tissue.

These and other aspects, embodiments and advantages will become more apparent when read with the detailed description and figures that follow.

DETAILED DESCRIPTION OF THE INVENTION

In one embodiment, the present disclosure provides a method for performing a piotomy on a mammal such as a human or non-human primate, the method comprising:

performing a craniotomy to remove the skull and expose dura mater;

removing the dura mater and arachnoid mater to expose subarachnoid space; and performing a piotomy using a laser to create a hole and expose the cerebral cortex.

The human brain is disposed within a bony housing known as the cranium. The cranium serves to protect the brain from injury. Between the cranium and brain is the meninges, which consist of three layers of tissue that cover and protect the brain and spinal cord. From the outermost layer toward the brain is the 1) dura mater, 2) arachnoid mater and 3) the pia mater.

Figure 1:
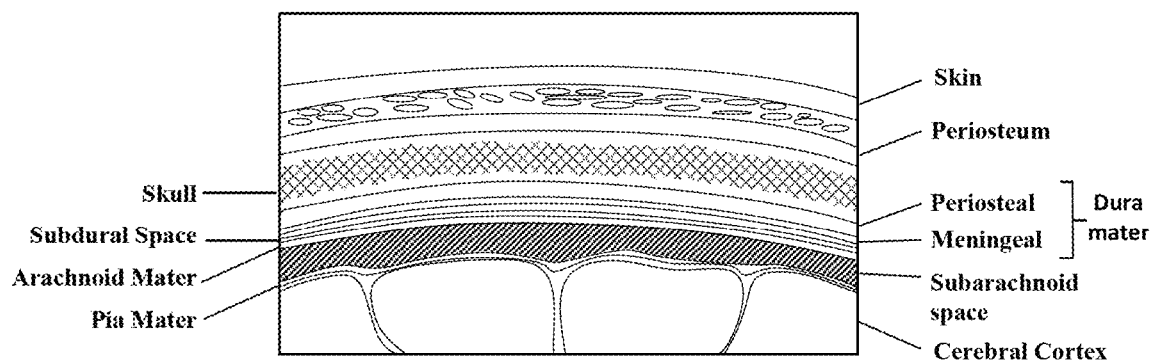
FIG. 1 is a cross-section of the skull and meninges.

FIG. 1 is a cross-sectional view of a mammalian brain. In one embodiment, the methods includes forming an opening in the scalp and cutting a hole through the skull and through the dura mater. The dura mater is made up of two layers known as the periosteum and the meningeal, which are generally referred to as only one layer or the dura layer. Next is the arachnoid layer. The arachnoid layer is a thin membrane that surrounds the brain and is separable from the dura. There is a space between the dura and the arachnoid membrane that is called the subdural space.

Below the arachnoid layer is the subarachnoid space, which is limited externally by a water-tight layer of connective tissue, the arachnoid, and internally by a thinner layer, the pia mater. It is within the subarachnoid space that CSF flows.

The pia mater adheres intimately to the surface of the brain and spinal cord. The pia mater is the layer of meninges closest to the surface of the brain. The pia mater has many blood vessels that reach deep into the surface of the brain. The major arteries supplying the brain provide the pia with its blood vessels. The space that separates the arachnoid and the pia mater is called the subarachnoid space.

The present disclosure provides an apparatus having a laser that emits at least one pulse or pulse train of laser energy and a fiber optical conduit for conducting the emitted pulse or pulse train of laser energy to a localized area of a subject's brain (e.g., human) to irradiate the localized area and ablate pia mater.

Advantageously, performing a piotomy using a laser to create a hole and expose the cerebral cortex allows for insertion of implantable devices in brain tissue. The insertion of implantable device such as a needle and/or electrode become much more facile and occurs without dimpling. Therefore, by reducing or eliminating any dimpling, the insertion process of an implantable device becomes much more efficient.

Figure 2:
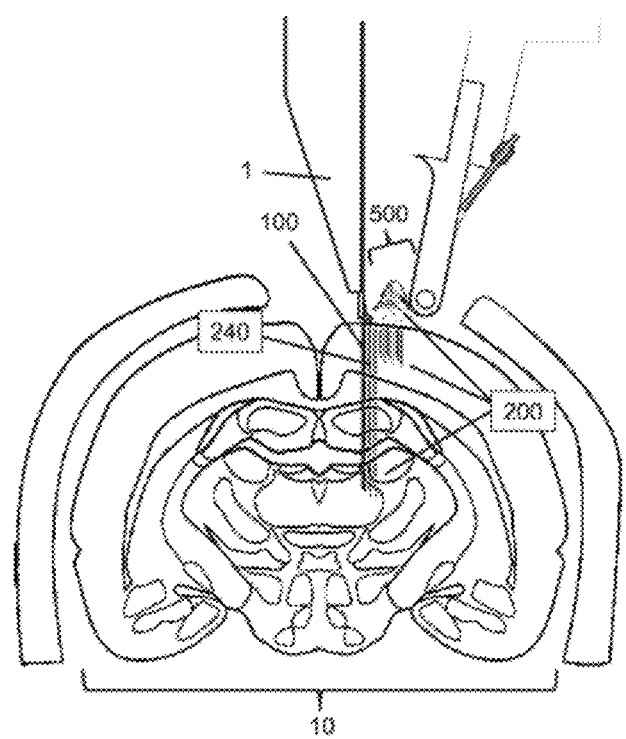
FIG. 2 is a prior art device for implanting electrodes into neurological tissue.

FIG. 2 is an illustration of prior art device of the system disclosed in WO 2016/126340 incorporated herein by reference. The system comprises i) microfabricated electrodes, ii) an inserter needle, and iii) an inserter robot. FIG. 2 shows a plurality of implantable devices 200 being implanted into a biological tissue 10 (e.g., a brain as depicted). An insertion device 1 manipulates an insertion needle 100 to engage an implantable device 200 from a cartridge 500 that includes a plurality of implantable devices. The device-loaded insertion needle is inserted into the brain 10 to a desired depth (which, as depicted, can be independently determined for each implantable device 200 that is implanted). The insertion needle 100 is then retracted, thereby disengaging the implantable device 200 from the insertion needle 100 and allowing the implantable device 200 to remain implanted in the biological tissue 10. In the depicted embodiment, each implantable device 200 includes a conduit (e.g., an electrode, waveguide) that is in communication with an external device (not shown) via a wire or fiber 240.

However, a consequence of using a needle (or blunt needle) on brain tissue without removal of the pia mater may result in the presence of dimples or blood tracks associated with the insertion process. Needle dimples may slow the insertion process. By removing the pia via the piotomy methods and apparatus disclosed herein, the insertion becomes much more facile without dimpling and is more efficient.

Before insertion of the needle, a laser hole is drilled through the pia mater surrounding the cerebral cortex. This laser hole reduces the force caused by the needle, and therefore needle insertion occurs faster, is more reliable and the needle hits the exact target much better than without the piotomy.

In certain aspects, the laser vaporizes water in the pia mater to ablate the tissue and create a hole in the pia. As water has high absorbance at approximate wavelengths of 2 μm, 3 μm and 10.6 μm, lasers having these same wavelengths can be used in the apparatus and methods of the present disclosure. In one aspect, a 2 μm wavelength laser is used.

In certain aspects, a continuous wave powered laser is used. In other aspects, a pulsed powered laser is used.

In certain aspects, the pulse of laser energy emitted by a laser having a wavelength of 2 μm is coupled to an optical conduit such as a fiber optic cable. A fiber optic cable is a cable that contains strands of glass fibers inside an insulated casing. To confine the optical signal in the core, the refractive index of the core is greater than that of the cladding, which effectively guides the laser energy from one end of optical conduit to the other end of optical conduit with negligible loss of energy. Typically, the fiber optic cable has a length suitable for transmitting the pulse of laser energy from the laser to the area or vicinity of the pia mater to be ablated.

In one aspect, the fiber optic cable has a length of about 1 meter to about 30 meters, or about 2 meters to about 15 meters, or about 3 meters to about 10 meters such as 6.5 meters. In another aspect, the fiber optic cable has a length of about 1, 2, 3, 4, 5, 6, 7, 8, 9 or 10 meters.

In certain aspects, the laser energy transmitted through the optical conduit from the laser at a particular region of the subject's brain can likewise be accomplished by providing an optical element or a series of optical elements that can be manipulated and adjusted relative to each other to achieve the desired focal point at a desired distance away relative to the end effector of the fiber cable. The apparatus may comprise control circuitry that is communicatively coupled to a laser. Control circuitry can control the output of the laser such as pulse duration of the laser, the number of pulses per unit of time, the total number of pulses and the power of laser emission. In certain aspects, the millisecond train of pulses are dynamically controlled and changed.

In certain aspects, a pulsed powered laser is used. For example, the pulse width can be about 1 nanosecond (ns) to about 100 nanoseconds (ns). In certain aspects, the pulse width can be about 10 nanoseconds to about 50 nanoseconds, or about 15 nanoseconds to about 45 nanoseconds, or about 30 nanoseconds in width. In certain aspects, the pulse width is about 1 ns, about 2 ns, about 3 ns, about 4 ns, about 5 ns, about 6 ns, about 7 ns, about 8 ns, about 9 ns, about 10 ns, about 11 ns, about 12 ns, about 13 ns, about 14 ns, about 15 ns, about 16 ns, about 17 ns, about 18 ns, about 19 ns, about 20 ns, about 21 ns, about 22 ns, about 23 ns, about 24 ns, about 25 ns, about 26 ns, about 27 ns, about 28 ns, about 29 ns, about 30 ns, about 31 ns, about 32 ns, about 33 ns, about 34 ns, about 35 ns, about 36 ns, about 37 ns, about 38 ns, about 39 ns, about 40 ns, about 41 ns, about 42 ns, about 43 ns, about 44 ns, about 45 ns, about 46 ns, about 47 ns, about 48 ns, about 49 ns, about 50 ns, about 51 ns, about 52 ns, about 53 ns, about 54 ns, about 55 ns, about 56 ns, about 57 ns, about 58 ns, about 59 ns, about 60 ns, about 61 ns, about 62 ns, about 63 ns, about 64 ns, about 65 ns, about 66 ns, about 67 ns, about 68 ns, about 69 ns, about 70 ns, about 71 ns, about 72 ns, about 73 ns, about 74 ns, about 75 ns, about 76 ns, about 77 ns, about 78 ns, about 79 ns, about 80 ns, about 81 ns, about 82 ns, about 83 ns, about 84 ns, about 85 ns, about 86 ns, about 87 ns, about 88 ns, about 89 ns, about 90 ns, about 91 ns, about 92 ns, about 93 ns, about 94 ns, about 95 ns, about 96 ns, about 97 ns, about 98 ns, about 99 ns, and/or about 100 ns.

In certain aspects, there is a 30-500 millisecond (ms) pulse train of 10 nanoseconds to about 50 nanoseconds pulses. In one aspect, there is a 100, 200, 300, 400, or 500 ms pulse train of 10 nanoseconds to about 50 nanoseconds pulses. For example, in one aspect, there is 208 ms of 30 ns pulses.

In certain aspects, each pulse delivers about 50 µJ to about 500 µJ of energy such as about 50, 55, 60, 65, 70, 75, 80, 85, 90, 95, 100, 200, 250, 300, 350, 400, 450 or about 500 µJ per pulse. In certain aspects, each pulse delivers about 100 µJ to about 500 µJ per pulse. In certain aspects, each pulse delivers about 100 to 500 µJ, or about 200 to 300 µJ, or about 300 to 500 µJ or about 400-500 µJ per pulse.

In certain aspects, a pulsed powered laser has a frequency or pulse rate of about 1 kHz to about 100 kHz. In certain aspects, the pulse has a frequency of about 10 kHz to about 50 kHz, or about 15 kHz to about 45 kHz, or about 33 KHz. In certain aspects, a pulsed powered laser has a frequency or pulse rate of about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, about 20 kHz, about 21 kHz, about 22 kHz, about 23 kHz, about 24 kHz, about 25 kHz, about 26 kHz, about 27 kHz, about 28 kHz, about 29 kHz, about 30 kHz, about 31 kHz, about 32 kHz, about 33 kHz, about 34 kHz, about 35 kHz, about 36 kHz, about 37 kHz, about 38 kHz, about 39 kHz, about 40 kHz, about 41 kHz, about 42 kHz, about 43 kHz, about 44 kHz, about 45 kHz, about 46 kHz, about 47 kHz, about 48 kHz, about 49 kHz, about 50 kHz, about 51 kHz, about 52 kHz, about 53 kHz, about 54 kHz, about 55 kHz, about 56 kHz, about 57 kHz, about 58 kHz, about 59 kHz, about 60 kHz, about 61 kHz, about 62 kHz, about 63 kHz, about 64 kHz, about 65 kHz, about 66 kHz, about 67 kHz, about 68 kHz, about 69 kHz, about 70 kHz, about 71 kHz, about 72 kHz, about 73 kHz, about 74 kHz, about 75 kHz, about 76 kHz, about 77 kHz, about 78 kHz, about 79 kHz, about 80 kHz, about 81 kHz, about 82 kHz, about 83 kHz, about 84 kHz, about 85 kHz, about 86 kHz, about 87 kHz, about 88 kHz, about 89 kHz, about 90 kHz, about 91 kHz, about 92 kHz, about 93 kHz, about 94 kHz, about 95 kHz, about 96 kHz, about 97 kHz, about 98 kHz, about 99 kHz, and/or about 100 kHz.

In certain aspects, the laser source generates about 0.5 watt to about 15 watts of average power. In certain aspects, the laser source generates about 10 watts such as about 10.5 of average power watts. In certain aspects, the laser source generates 0.5 watt to about 10 watts of power, such as about 2 watts, about 3 watts, about 4 watts, about 5 watts, about 6 watts, about 7 watts, about 8 watts, about 9 watts, about 10 watts, about 11 watts, about 12 watts, about 13 watts, about 14 watts, about 15 watts of average power.

In certain aspects, the disclosed apparatus is configured and adapted to display data indicative of a result obtained by processing the light captured by a feedback optical channel. The disclosed apparatus is configured and adapted to receive input from a user regarding control of the laser regarding the pulse duration, the power of each laser energy pulse emitted, the number of pulses per unit of time, the total number of pulses. In certain aspects, the laser can be controlled such that the volume of affected tissue ablation is about 10 µm to about 500 µm or about 75 µm to about 200 µm. The pia mater is approximately 100 µm thick.

In certain aspects, the LightScalpel LS-1005 or LS-2010 carbon dioxide laser system can be used, which is intended for use in surgical procedures such as incision, excision, vaporization, ablation, or coagulation of soft tissue. The LightScalpel has a wavelength 10.6 µm.

An in vitro model was used to test the system and methods of the present disclosure. In one aspect, the model used was 0.6% Agar mold with a collagen sheet (~100 µm thickness) stretched over top. The agar was placed in a Petri dish and molded using a 'flipped' agar method (molded into a lid, flipped into base), and collagen stretched over entire Petri dish. The data in Table 1 below used a 355 nm wavelength laser.

TABLE 1

| Number | Rep Rate (Hz, or #bursts/sec) | #pulses | reported pulse energy (µJ) | Actual pulse Energy (µJ) | Total Energy (µJ) | Location (X,Y) (µm) |
| --- | --- | --- | --- | --- | --- | --- |
| 1 | 10,000 | 5000 | 98.3 | 61.9 | 309673.4 | 0, 0 |
| 2 | 10,000 | 5000 | 96 | 60.5 | 302427.7 | 2000, 0 |
| 3 | 10,000 | 5000 | 99.7 | 62.8 | 314083.8 | 4000, 0 |
| 4 | 10,000 | 5000 | 98.5 | 62.1 | 310303.5 | 0, 2000 |
| 5 | 10,000 | 5000 | 98.4 | 62 | 309988.4 | 2000, 2000 |
| 6 | 10,000 | 3500 | 97.2 | 61.2 | 214345.7 | 4000, 2000 |
| 7 | 10,000 | 3500 | 97 | 61.1 | 213904.6 | 0, 4000 |
| 8 | 10,000 | 3500 | 99.8 | 62.9 | 220079.2 | 2000, 4000 |
| 9 | 10,000 | 3500 | 98 | 61.7 | 216109.8 | 4000, 4000 |

Actual pulse energy calculated based on calibration of system with power meter
Total amount of energy delivered is (pulse energy) * (#pulses)
Time of ablation is (#pulses)/(rep rate)

Figure 3:
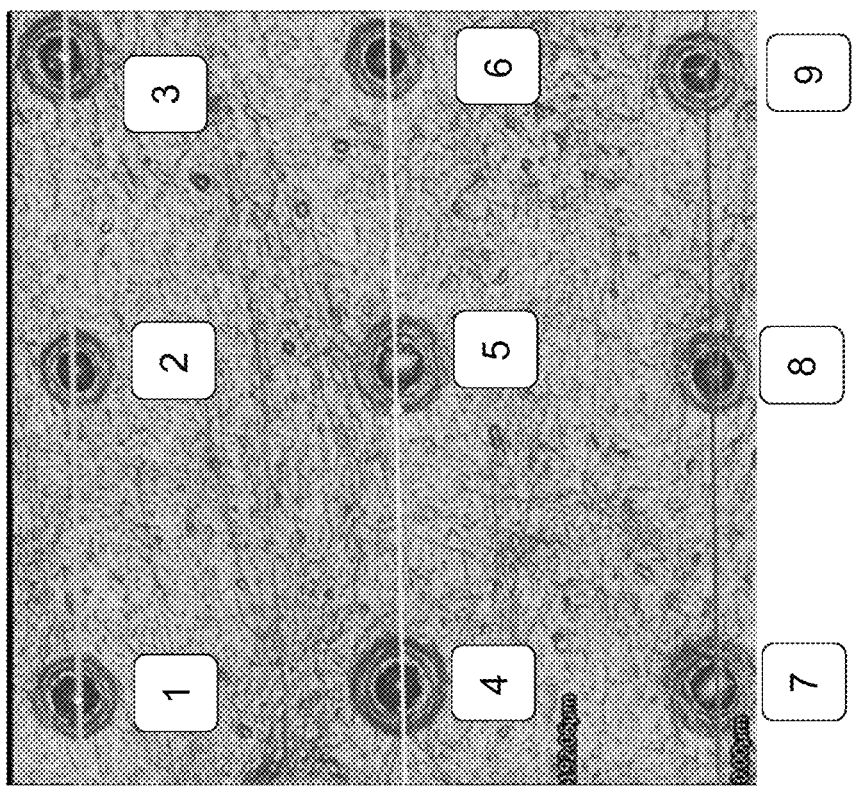
FIG. 3 illustrates an embodiment of the present disclosure.

FIG. 3 shows the 9 holes made using the inventive apparatus and methods. When tested with a needle, there was no dimpling with the insertion of a needle. Without dimpling, the insertion of an implantable device such as a needle becomes much more facile. As such, it is expected that the insertion of the needle in vivo will not cause dimpling and will be much more efficient.

All publications and patent applications cited in this specification are herein incorporated by reference as if each individual publication or patent application were specifically and individually indicated to be incorporated by reference. Although the foregoing disclosure has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for performing a piotomy on a mammal prior to insertion of an implantable device, the method comprising:
    performing a craniotomy to remove the skull and expose dura mater;
    removing the dura mater and arachnoid mater to expose subarachnoid space;
    performing a piotomy using a laser, which laser generates between 2 watts and 15 watts of power, to create a hole and expose the cerebral cortex; and
    inserting a needle and thereafter the implantable device into the hole without dimpling.

2. The method of claim 1, wherein the mammal is a non-human primate.

3. The method of claim 1, wherein the mammal is a human.

4. The method of claim 1, wherein the laser has a wavelength of about a 350 nm to about 10.6 µm.

5. The method of claim 1, wherein the laser is a 2 µm wavelength laser.

6. The method of claim 1, wherein the laser vaporizes water in the pia mater to ablate the tissue and create the hole.

7. The method of claim 1, wherein the laser is a pulsed powered laser.

8. The method of claim 1, wherein the laser source has average power of about 10 watts or 10.5 watts.

9. The method of claim 1, wherein the pulse has a width of about 10 nanoseconds to about 50 nanoseconds.

10. The method of claim 1, wherein the pulse has a frequency of about 10 kHz to about 50 kHz.

11. The method of claim 1, wherein the subarachnoid space is suctioned before performing the piotomy using a laser.

12. A method for performing a piotomy on a mammal, prior to insertion of an implantable device, the method comprising:
    performing a craniotomy to remove the skull and expose dura mater;
    removing the dura mater and arachnoid mater to expose subarachnoid space;
    performing a piotomy using a laser coupled to a fiber optic cable, which generates between 2 watts and 15 watts of power, to create a hole and expose the cerebral cortex, wherein the laser vaporizes water in the pia mater to ablate the tissue to create the hole; and
    inserting a needle and thereafter the implantable device into the hole without dimpling.

13. The method of claim 12, wherein the mammal is a non-human primate.

14. The method of claim 12, wherein the laser has a wavelength of about a 350 nm to about 10.6 μm.

15. The method of claim 12, wherein the laser source has average power of about 10 watts or 10.5 watts.

16. The method of claim 12, wherein the pulse has a width of about 10 nanoseconds to about 50 nanoseconds.

17. The method of claim 12, wherein the pulse has a frequency of about 10 kHz to about 50 kHz.

18. The method of claim 12, wherein the subarachnoid space is suctioned before performing the piotomy using a laser.

* * * * *